United States Patent [19]

Kumakura et al.

[11] Patent Number: 4,692,935
[45] Date of Patent: Sep. 8, 1987

[54] AUTOMATIC STEEL ANALYSIS APPARATUS

[75] Inventors: Koichi Kumakura; Akira Ryuzono; Yoshinori Hosokawa, all of Kyoto, Japan

[73] Assignee: Horiba, Ltd., Kyoto, Japan

[21] Appl. No.: 803,214

[22] Filed: Nov. 27, 1985

[30] Foreign Application Priority Data

Nov. 28, 1984 [JP] Japan .................... 59-252596

[51] Int. Cl.[4] .................... G01N 23/223
[52] U.S. Cl. .................... 378/49; 378/44; 378/45
[58] Field of Search .................... 378/44, 45, 46, 47, 378/48, 49, 50, 160; 250/505.1, 359.1

[56] References Cited

U.S. PATENT DOCUMENTS 3,119,019 1/1964 Henry, Jr. et al. .................... 250/359.1
3,141,976 7/1964 MacIntyre .................... 378/160

FOREIGN PATENT DOCUMENTS 0072684 6/1978 Japan .................... 378/49

Primary Examiner—Janice A. Howell
Assistant Examiner—David P. Porta
Attorney, Agent, or Firm—Wenderoth, Lind & Ponack

[57] ABSTRACT

An automatic steel analysis apparatus for analyzing the composition of steel materials by carrying out an element analysis using an X-ray excited energy dispersion type fluorescent analysis in the conveying path of the steel materials. A movable housing is vertically movably mounted below the conveying path and has a window in the top thereof closed by an X-ray permeable membrane. An X-ray tube and a semiconductor detection element are housed in the movable housing, and the detection element is connected to a computing apparatus for supplying analysis information thereto for enabling the computing apparatus to determine the composition of steel materials. An air conditioning apparatus controls the temperature and humidity within the movable housing. A leaded rubber packing is mounted around the outside of the window for engaging with the under side of the steel material located in the conveying path when said housing is raised, and an openable and closable protective shutter is mounted on the housing and movable between a position in which it covers said window to protect the X-ray permeable membrane and a position away from the window and in which the window is uncovered. A sensor connected with the leaded rubber packing senses the engagement of the leaded rubber packing with the under side of a steel material, and an X-ray shutter opens to expose the X-ray tube for a predetermined time sufficient for carrying out analysis in response to the sensing by the sensor of the engagement of the leaded rubber packing with a steel material.

4 Claims, 8 Drawing Figures

AUTOMATIC STEEL ANALYSIS APPARATUS

BACKGROUND OF THE INVENTION

1. Field of the Invention

The present invention relates to an automatic steel analysis apparatus for analyzing the composition of steel materials by carrying out an element analysis using an X-ray excited energy dispersion type fluorescent analysis positioned along the path of conveyance of such steel materials and which is useful for checking the composition of stainless steel plates directly before the shearing step in the harsh environment of a stainless steel plate production line and the like.

2. Description of the Prior Art

An apparatus for analyzing the composition of stainless steel plates directly before the shearing step in a stainless steel plate production line, in which an analysis for the elements in the steel has been heretofore carried out by a radio-isotope excited energy dispersion type fluorescent analysis.

However, such apparatus has disadvantages in that not only is it difficult to control from the standpoint of safety, since a large dose of radio-isotope is required, but also where it is necessary to analyze for a plurality of elements, such as nickel, chromium, copper, molybdenum and titanium, as many kinds of radio-isotopes as there are elements are required, and as many detectors as there are radio-isotopes are required, since only one kind of element can be analyzed for by one kind of radio-isotope. Therefore, the apparatus is large-sized and complicated.

SUMMARY OF THE INVENTION

It is an object of the present invention to provide an automatic steel analyzing apparatus from which the above described disadvantages incidental to the conventional apparatus are eliminated, and which is easy to control from the standpoint of safety, which is small-sized so that it is suitable for the incorporation in the stainless steel plate production line, and which is capable of carrying out a stable analysis without being influenced by dust, changes in temperature and humidity and the like, even in the unstable environment of a stainless steel production line.

In order to achieve the above described object, an apparatus according to the present invention is provided which is adapted to distinguish the composition of steel materials by carrying out an element analysis by using an X-ray excited energy dispersion type fluorescent analysis at a position along the path along which said steel materials are conveyed during production, which apparatus is characterized by a housing having therein a window formed of an X-ray permeable membrane on the upper side of the path and housing a detector consisting of an X-ray tube, and a semiconductor detection element provided below the path of conveyance, said housing being movable up and down relative to body and having therein a detected signal computing apparatus and an air conditioner for controlling the temperature and the humidity within said housing and provided with a leaded rubber packing, which is positioned around said window and which engages the under side of steel materials located in the conveying path when said housing is raised, and an openable and closable protective shutter in the upper portion of said housing for covering said window to protect said X-ray permeable membrane only when said housing is located at the descended position thereof, a sensor for detecting the adherence of said leaded rubber packing to the under side of the steel material, and said X-ray shutter being opened at a time depending upon the detected position.

In the apparatus having the above described construction, the housing is located at the descended position thereof at times other than when an analysis is being conducted, and damage to the X-ray permeable membrane and the detecting means within the housing due to steel material falling and contacting the membrane and the detecting means is prevented by the protective shutter. During analysis, the protective shutter is opened after the housing is raised. At this time, since the X-ray shutter is closed until the leaded rubber packing is adhered to the under side of the steel material, X-rays can be prevented from leaking out while the case goes up and down even though the X-ray tube is operating. In addition, when steel material is not located at the position of the apparatus along the conveying path, the leaded rubber packing is not adhered to the under side of of the steel material, so that the absence of the steel material is detected by the sensor, so that the X-ray shutter is opened only when steel material is located at the position of the apparatus along the conveying path. In short, the leaded rubber packing is adhered to the under side of the steel material without fail and the X-ray shutter is opened, so that X-rays do not leak out even though the X-ray shutter is opened. In addition, the detecting portion is housed in a housing temperature and humidity within which are controlled, so that a stable analysis can be carried out.

BRIEF DESCRIPTION OF THE DRAWINGS

The invention will be described in greater detail in connection with a preferred embodiment of the present invention, and in which.

DESCRIPTION OF THE PREFERRED EMBODIMENT

Figure 1:
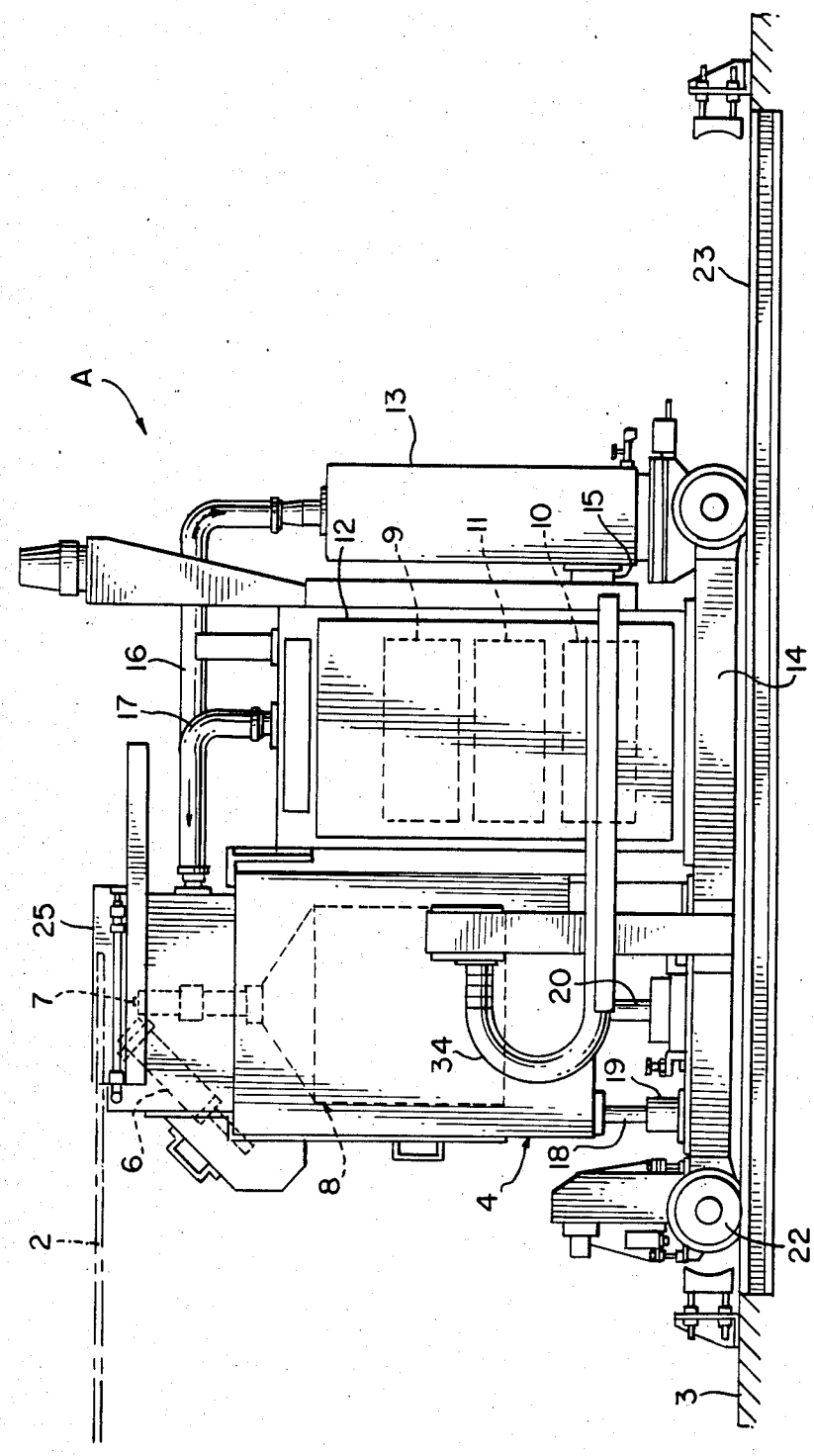
FIG. 1 is a side view of the apparatus according to the invention.
Figure 2:
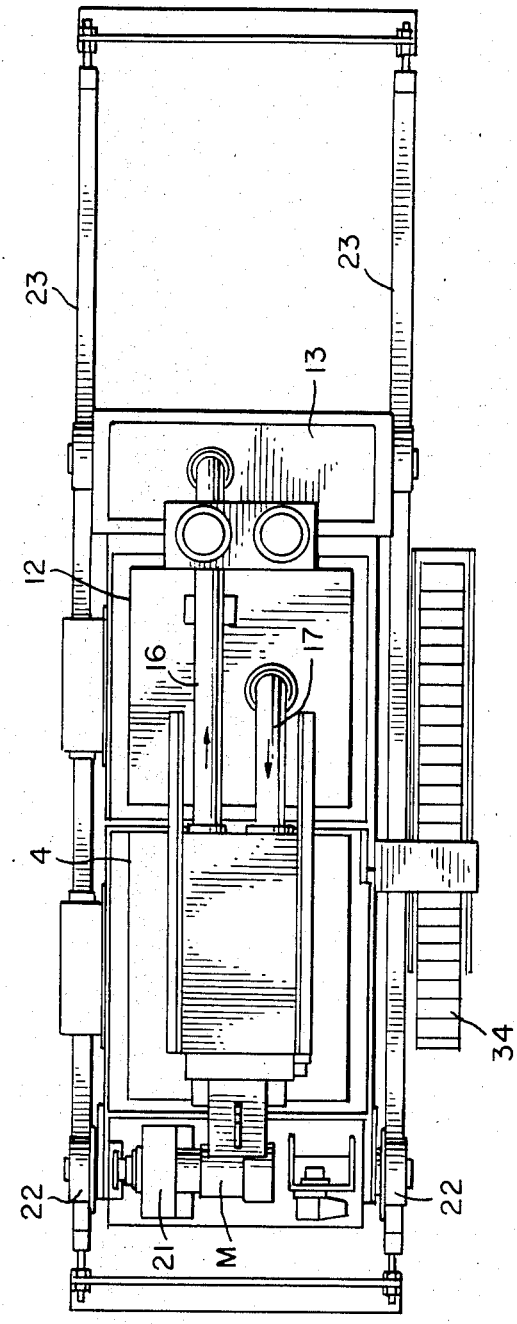
FIG. 2 is a plan view thereof.
Figure 4:
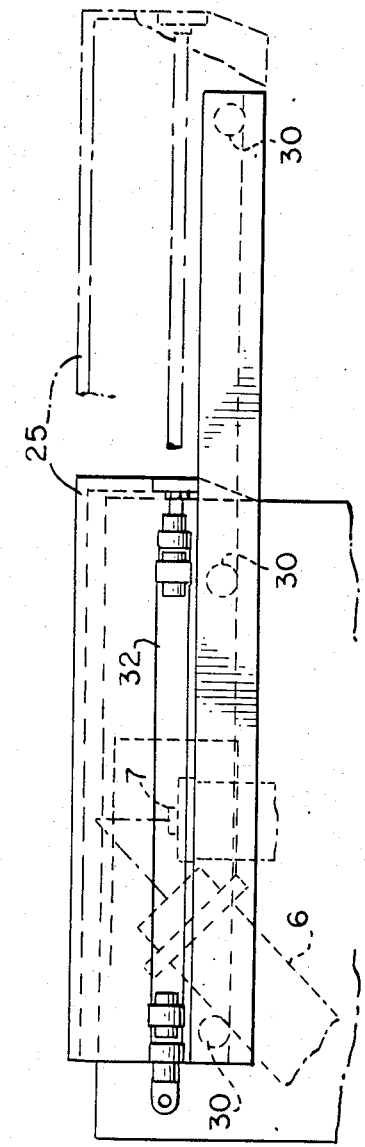
FIG. 4 is a diagrammatic side view of the principal parts of the apparatus.
Figure 3:
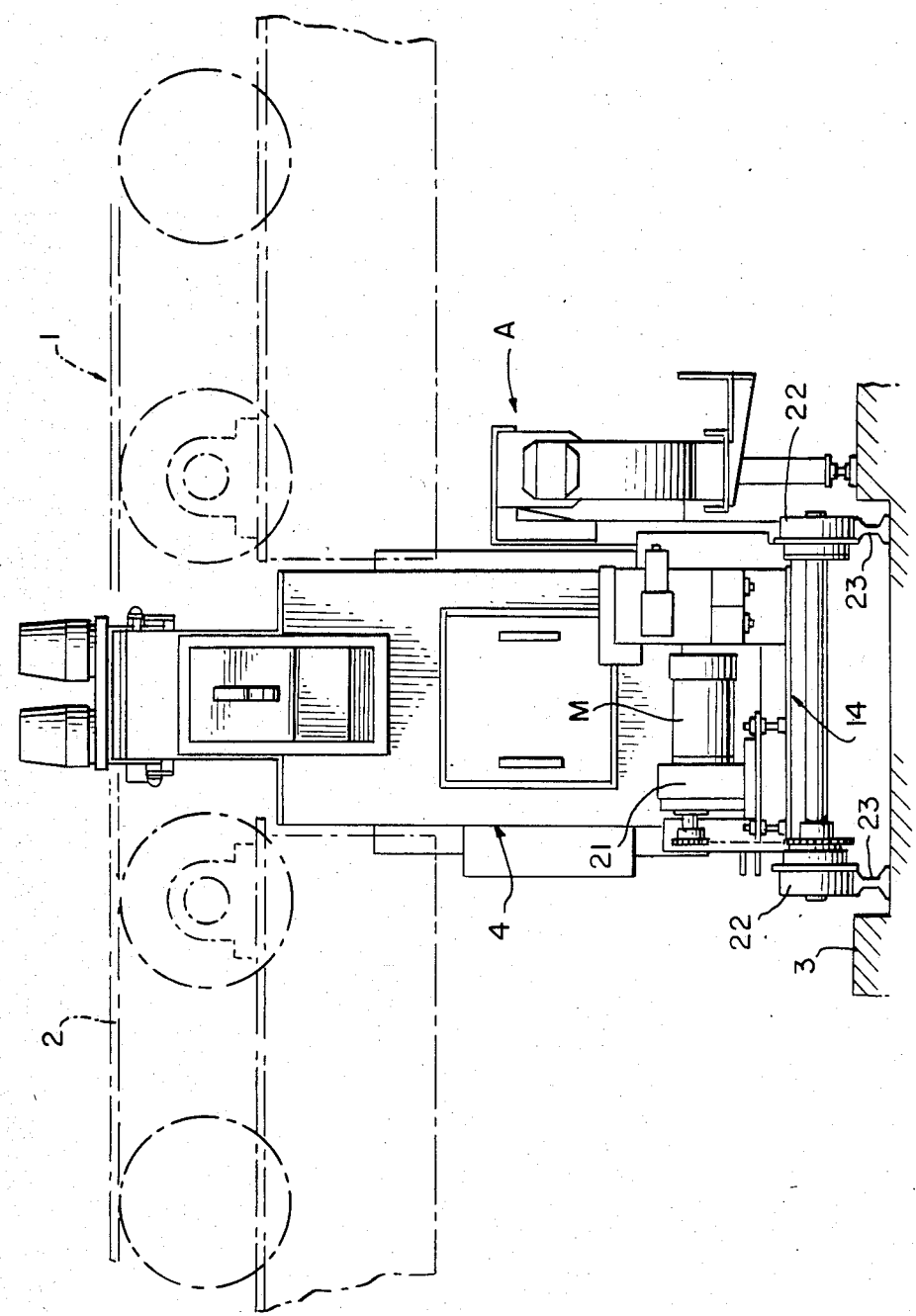
FIG. 3 is a front view thereof.
Figure 5:
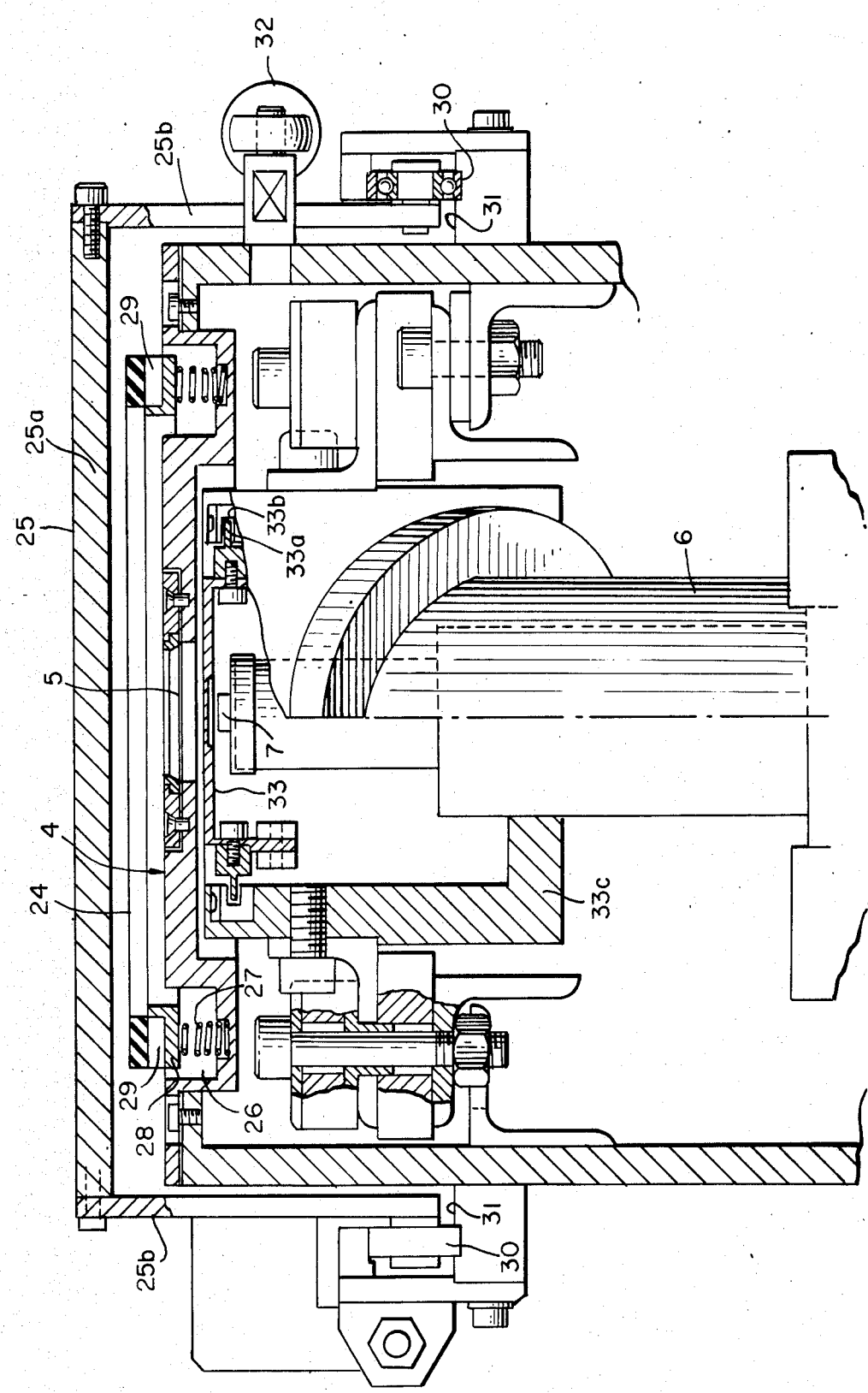
FIG. 5 is a longitudinal sectional view of a principal part of the apparatus.

Referring now to FIGS. 1 to 3 showing the overall automatic steel analysis apparatus according to the present invention, and FIGS. 4 and 5 showing the principal parts of said apparatus, a steel material 2 such as a stainless steel plate is conveyed along a conveying path 1 by a conveyor (not shown) disposed at the suitable height above a floor surface 3 or the like. The automatic steel analysis apparatus A for analyzing the steel material 2 by an element analysis using an X-ray excited energy dispersion type fluorescent analysis is provided at a position along the conveying path 1, for example directly ahead of a shearing apparatus (not shown).

The automatic steel analysis apparatus has a movable housing 4 provided with a window 5 (visible in FIG. 5) formed of an X-ray permeable polyester membrane, for example of polyester sold under the trademark MYLAR by E. I. DuPont de Nemours, Wilmington, Del., formed on the upper side thereof and housing a detector means 8 consisting of an X-ray tube 6 and a semiconductor detection element 7 therein. Said housing 4 is movable up and down on a body 14 on which is mounted computing apparatus 9 for determining the steel composition from the information from said detector means 8, a high-tension power source 10, an X-ray tube control power source 11 and the like housed in a fixed housing 12, and an air conditioner 13. The air conditioner 13 is connected with the fixed housing 12 by a duct 15, and with the movable housing 4 by a flexible duct 16, and the movable housing 4 is connected to the fixed housing 12 by a further flexible duct 17. The temperature and humidity within the movable housing 4 and the fixed housing 12 are held constant by circulating nitrogen gas, the temperature and humidity of which are adjusted by the air conditioner 13, through the duct 15, the fixed housing 12, the flexible duct 17, the movable housing 4 and the flexible duct 16 in this order. Vertical guide shafts 18 are mounted at the four corners of the bottom plate of the movable housing 4 and slide vertically in bearing housings 19 mounted on the body 14. An air piston-cylinder device 20 is connected between the central portion of the bottom plate and the body 14 for moving the housing 4 up and down.

In addition, the body 14 has wheels 22 thereon rolling on rails 23 laid on the floor surface 3 at right angles to the conveying path 1. At least one of the wheels 22 is driven by a motor M on the body 14 through reduction gear means 21. Said housing 4 is disposed below the conveying path 1 during normal operation condition and the body 14 is moved to the desired lateral position of the conveying path 1 so as to provide a sufficient operating space therearound. A cable bundle 34 for a wiring harness and gas piping is connected to the housing 12.

Said movable housing 4 is provided with a leaded rubber packing 24, (visible in FIG. 5) which is positioned around said window 5 and which is pressed against the under side of the steel material 2 located in the conveying path 1 when the movable housing 4 is raised, and an openable and closable protective shutter 25 at the upper part thereof for covering said window 5 to protect said X-ray permeable membrane only when said movable housing 4 is located at the lowered position thereof. Although the movable housing 4 can have the leaded rubber packing 24 mounted on the upper portion thereof in various ways, in this embodiment as shown in FIG. 5, the movable housing 4 is provided with an annular groove 26 having a square shape in plan view in the ceiling plate thereof, said annular groove 26 having a metallic square-shaped annular frame 28 resiliently supported on springs 27 on the bottom surface thereof, and said square-shaped annular frame 28 being provided with a square-shaped leaded rubber packing 24 fixedly adhered to the upper surface thereof by means of adhesive or the like. A sensor 29 for detecting the contact of the leaded rubber packing 24 with the under side of the steel material is provided at each of two places on opposite sides of said square-shaped annular frame 28 with said window 5 as a center. Although a pressure switch may be used as the detector 29, a non-contact type switch is preferably used. Accordingly, in this embodiment, a high-frequency induction type proximity switch is used.

Said protective shutter 25, as shown in FIGS. 4 and 5, is composed of a horizontal plate portion 25a and a pair of leg plate portions 25b extending down from both ends thereof, said leg plate portions being provided with a plurality of rollers 30 rotatably mounted on the lower ends thereof for moving said protective shutter 25 along rails 31 mounted on opposite sides of the movable housing 4. The shutter is driven along the rails 31 by a horizontal air piston-cylinder means 32 extending from one end of the housing 4 to the side of a leg plate portion 25b.

Said movable housing 4 is provided with an openable and closable X-ray shutter 33 disposed below said window 5, as shown in FIG. 5 having members 33a slidable in grooves 33b in a casing surrounding the upper end of X-ray tube 6 and detection element 7 and driven by drive means (not shown) similar to that for protective shutter 25. Said sensor 29 detects the tight engagement of said leaded rubber packing 24 with the under side of the steel material 2 located at the appointed position in the conveying path 1 and said X-ray shutter 33 is opened for the desired time (for example, several to ten seconds) depending on the basis of the result being tested for.

The operation of the above described automatic steel analysis apparatus will be described below.

Figure 6A:
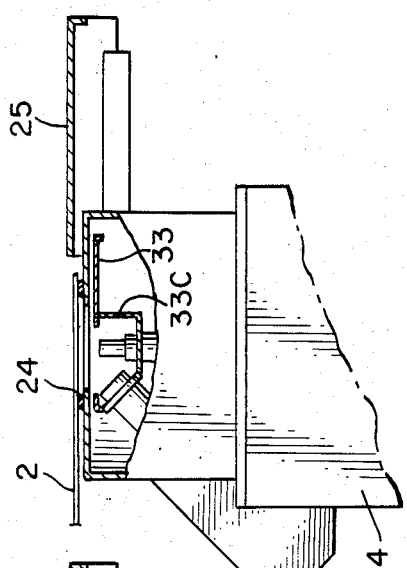
FIGS. 6(A), 6(B) and 6(C) are diagrammatic views showing the operation of the apparatus.

The steel material 2 being transferred along the conveying path 1 is stopped at a predetermined position above the position of the movable housing 4. At this time, the housing 4 is in readiness in the lowered position with the protective shutter 25 closed, as shown in FIG. 6A.

Figure 6B:
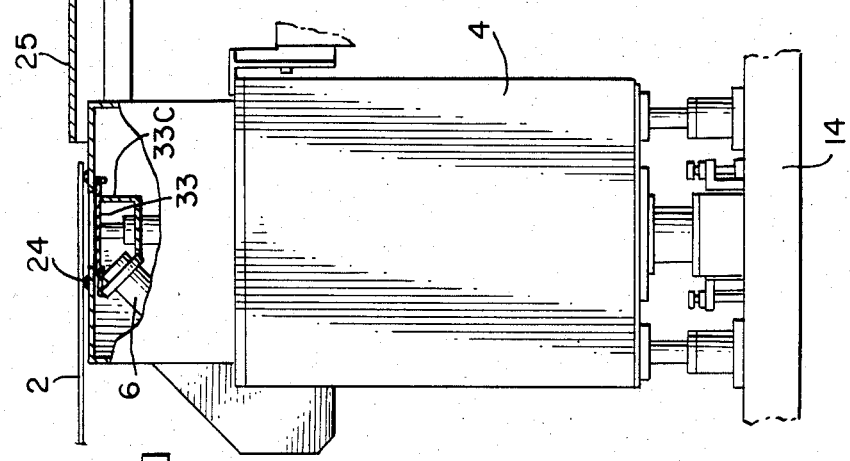
Figure 6C:
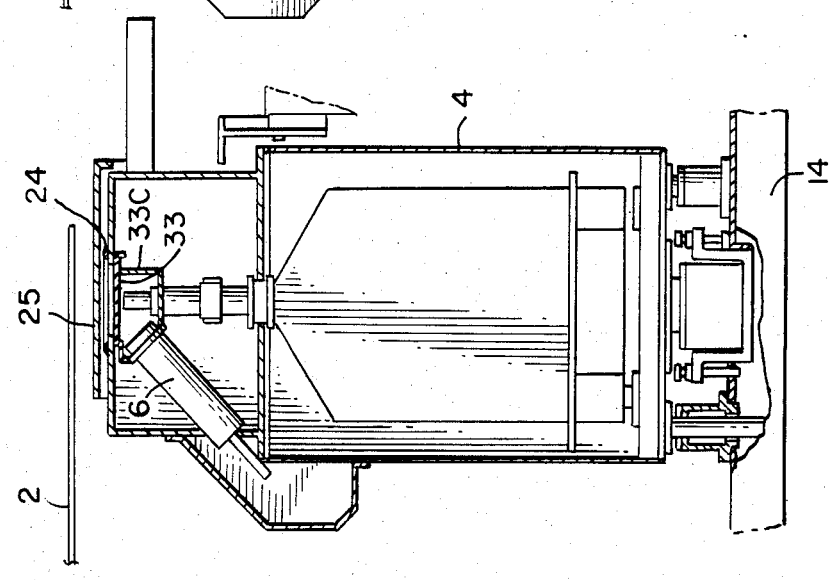

The kind of steel (the kind of steel to be subjected to the working process such as shearing in the subsequent step) is set on a control panel (not shown) and then a measurement switch (not shown) on the control panel is pushed. As a result, the automatic analysis for the composition of the steel is carried out. First, the protective shutter 25 is opened by the operation of the piston-cylinder means 32, and the movable housing 4 is raised by the piston-cylinder means 20 in respect to the switching on of said measurement switch, as shown in FIG. 6B. Upon the engagement of the leaded rubber packing 24 with the under side of the steel material 2, the sensor 29 emits a signal which is used to operate the drive means for the X-ray shutter 33 to open it, thereby permitting X-rays from the already operating X-ray tube 6 to strike the steel material 2 through the membrane 5 for starting the element analysis of the steel material 2 by an X-ray excited energy dispersion type fluorescent analysis, as shown in FIG. 6C. After the required number of seconds for the production of the emissions from the steel have passed, the X-ray shutter 33 is closed, the movable housing 4 is lowered, and the protective shutter 25 is closed. During this time the computing device analyzes the detected emissions for the kinds of elements such as nickel, chromium, copper, molybdenum and titanium which are present and which indicate the kind of steel present in the conveying path.

If the analytical result is "satisfactory", that is to say, it matches the kind of steel material 2 set on the control panel, the conveyance of the steel material 2 along the conveying path 1 is resumed to convey the steel material 2 to the subsequent process.

Because the apparatus according to the present invention has the above described construction and uses an X-ray excited energy dispersion type fluorescent analysis means as the analytical means, the apparatus is easy to control with respect to safety in comparison with an apparatus in which radio-isotopes are used, it can be kept small-sized, and the influence of the dispersion of surface roughness of the steel materials, the inclination of the surface of the steel material and the space between the surface of the steel material and the detector upon the analytical value is reduced.

Further, according to the present invention, since the detector is housed in a movable housing the temperature and humidity of which are controlled, and the movable housing being located in a lowered position during the times other than when an analysis is being made and the window is covered by a protective shutter, not only can the X-ray permeable membrane and the detector housed in the housing can be protected from damage by falling steel material or contact with the steel material moving in the conveying path and the like, but also a stable analysis can be carried out even in the unstable environment of the production line without being influenced by dust and any changes of the ambient temperature and humidity.

In addition, although the protective shutter is opened when the movable housing is raised when an analysis is to be carried out, the X-ray shutter remains closed until the leaded rubber packing engages the under side of the steel material located in the conveying path, so that X-rays are prevented from leaking out during the time the movable housing is moving up and down, even though the X-ray tube remains in the operative condition so that the analysis of the kind of steel can be efficiently and continuously carried out on the production line. When there is no steel material in the conveying path, the leaded rubber packing is not adhered to the under side of the steel material, so that the absence of the steel material is detected by the sensor and the X-ray shutter is not opened. In other words, the X-ray shutter is opened only when the leaded rubber packing is engaged with the under side of the steel material, so that X-rays are prevented from leaking out when the X-ray shutter is opened.

Furthermore, the only portion of the apparatus which is brought into contact with the under side of the steel material is the leaded rubber packing, so that there is no possibility that the under side of the steel material will be damaged.

Thus, according to the present invention, an automatic steel analysis apparatus, which is suitable for incorporation into the production line for stainless steel plates and the like, has been provided.

What is claimed is:

1. An automatic steel analysis apparatus for analyzing the composition of steel materials moving along a conveying path in a harsh environment by carrying out an element analysis using an X-ray excited energy dispersion type fluorescent analysis along the conveying path of the steel materials, comprising:

a movable housing mounted on said apparatus below the conveying path and having a window in the top thereof and an X-ray permeable membrane filling said window, said movable housing being mounted for vertical up and down movement toward and away from the conveying path;

a detector means consisting of an X-ray tube and a semiconductor detection element housed in said movable housing;

a computing apparatus to which said detection element is connected for supplying analysis information thereto for enabling said computing apparatus to determine the composition of steel materials;

an air conditioning apparatus connected to said movable housing for controlling the temperature and humidity within said movable housing;

a leaded rubber packing means mounted around the outside of said window for engaging with the under side of the steel material located in the conveying path when said housing is raised;

an openable and closable protective shutter mounted on said housing and movable between a position in which it covers said window to protect said X-ray permeable membrane and a position away from said window and in said window is uncovered;

a sensor connected with said leaded rubber packing means for sensing the engagement of said leaded rubber packing means with the under side of a steel material; and an X-ray shutter operatively associated with said X-ray tube and including means for opening said X-ray shutter for a predetermined time sufficient for carrying out analysis in response to the sensing by said sensor of the engagement of said leaded rubber packing means with a steel material.

2. The apparatus as claimed in claim 1 in which the top of said housing has an annular groove therein around said window which has a square shape when viewed in plan, and said leaded rubber packing means comprises a square frame resiliently mounted on the bottom of said groove and having a leaded rubber packing mounted on the upper surface thereof.

3. The apparatus as claimed in claim 1 in which said sensor is a high frequency induction type proximity switch.

4. The apparatus as claimed in claim 1 in which said movable housing has a casing therein surrounding the upper end of said X-ray tube and said detection element and on the top of which said X-ray shutter is slidable for opening and closing said casing for covering and exposing said X-ray tube and said detection element.

* * * * *